United States Patent [19]

Dörschug et al.

[11] Patent Number: 5,028,587
[45] Date of Patent: Jul. 2, 1991

[54] MIXED CRYSTALS OF INSULIN AND INSULIN DERIVATIVES

[75] Inventors: Michael Dörschug, Bochum; Rainer Obermeier, Hattersheim am Main, both of Fed. Rep. of Germany

[73] Assignee: Hoechst Aktiengesellschaft, Frankfurt am Main, Fed. Rep. of Germany

[21] Appl. No.: 196,530

[22] Filed: May 20, 1988

[30] Foreign Application Priority Data

May 22, 1987 [DE] Fed. Rep. of Germany ....... 3717370

[51] Int. Cl.$^5$ .................. A61K 37/26; C07K 7/40
[52] U.S. Cl. ................................. 514/3; 514/4; 530/303
[58] Field of Search ............... 514/3, 4; 530/303

[56] References Cited

U.S. PATENT DOCUMENTS

| 2,538,018 | 1/1951 | Krayenbohl | 514/3 |
| 4,608,364 | 8/1986 | Grau | 514/4 |
| 4,701,440 | 10/1987 | Grau | 514/3 |

FOREIGN PATENT DOCUMENTS 0132769 2/1985 European Pat. Off. .
0132770 2/1985 European Pat. Off. .
0140084 5/1985 European Pat. Off. .
1492837 11/1977 United Kingdom .

OTHER PUBLICATIONS

Doerschung, *Chemical Abstracts*, III, 427 (1989), abst. no. 160217q.
U.S. Ser. No. 06/650,639, Obermeier et al., filed Sep. 14, 1984.

*Primary Examiner*—F. T. Moezie
*Attorney, Agent, or Firm*—Finnegan, Henderson, Farabow, Garrett and Dunner

[57] ABSTRACT

Mixed crystals composed of (a) unmodified insulin, des-Phe-B1 insulin, des-Thr-B30 (human) or des-Ala-B30 (pork, beef) insulin and (b) least one insulin having a basic modification at the C-terminal end of the B chain, preferably composed of human insulin and Arg-B31 human insulin and/or $Arg_2$-(B31-32) human insulin. These mixed crystals are obtained by crystallization from aqueous solution within a narrow pH range (from about 5.5 to about 6.9). The mixed crystals show a specific moderately prolonged profile and are suitable for the treatment of diabetes mellitus.

5 Claims, No Drawings

MIXED CRYSTALS OF INSULIN AND INSULIN DERIVATIVES

Diabetes mellitus is a metabolic disorder in which the essential sign is a raised blood glucose level. It is caused by insufficient amounts of the pancreatic hormone insulin being released. As a rule, the replacement of the natural hormone is nowadays effected with animal insulin isolated from the glands of slaughtered livestock, or human insulin which can be obtained semisynthetically from pork insulin or by genetic engineering methods.

A consequence of the particular chemical nature of insulin is that parenteral therapy is the rule; on passage through the stomach and intestines, for example, the hormone would be completely broken down before exerting an effect. However, breakdown reactions, essentially by various, relatively unspecific, proteolytic enzymes, take place at the site of injection and in the circulation too. The short in vivo half-life of only about 7 minutes, which results from this, is in principle physiologically worthwhile, in the sense of homeostasis; however, this entails considerable difficulty for therapy because the diabetic has to inject up to four times a day, as a rule shortly before the meals.

Now a feature of diabetes therapy is the individual influencing factors, such as differences in the utilizability of the meals and differences in the characteristics of the subcutaneous tissue, together with, however, the specific eating habits, physical activity, and many others. It is thus indispensable for good blood glucose control to have available a number of insulin products which have different characteristics of action and are suitable for individual requirements. Non-optimal control has been suggested to be connected not only with the immediate subjective and objective effects, such as hyper- or hypoglycemic episodes, but also, and in particular, with the range of types of delayed diabetic damage. These include, in particular, macro- and microangiopathy, neuropathy, nephropathy and retinopathy.

Preparations which have proved to be suitable for the patient's requirements are not only pure prolonged insulins but, in particular, what are called intermediate insulins. They are mixtures of a prolonged and an immediate and short-acting component. Mixtures of this type are complicated multiphase systems which remain stable over long periods only in a relatively narrow range of mixing ratios. Thus, for example, a suspension of 2-zinc pork insulin crystals is not freely miscible with dissolved pork insulin. Because of the relatively high content of zinc necessary to stabilize the crystals, there is precipitation of the admixed dissolved insulin, either immediately or over the course of time. Mixtures of this type are stable within narrow limits when the dissolved insulin which is used is beef insulin (but this means a loss of the species purity which is a medically desired property) or a mixture of dissolved pork insulin and desphenylalanine(B1) pork insulin (GB-A-1,492,837). More advantageous in terms of the miscibility with dissolved insulin are protamine insulin formulations, where crystals composed of protamine and insulin in the isophane ratio are used as prolonging component. It is possible to use these products to prepare NPH (=neutral protamine formulation according to Hagedorn)-typical profiles of action. Although the presence of added protamine (as such or in salt form) appears defensible because protamine is a relatively innocuous exogenous protein, nevertheless it remains an exogenous substance which may result in undesired reactions, at least in patients who are particularly sensitive to exogenous proteins.

Hence it is important to prepare stable pharmaceutical agents which have characteristics of action which are suited to the individual requirements of the diabetic and which, moreover, contain only minimal amounts of exogenous auxiliaries, in particular only minimal amounts of exogenous proteins, or, which is best, no such substances whatever. In this respect, active substance combinations composed of unmodified insulin or its Des-Phe$^{B1}$ analog and of insulin derivatives whose B chain has a C-terminal organic group with basic properties represent a considerable advance (cf. for example EP-A 132,769).

Insulin derivatives which have at the C-terminal end of the B chain the residues Arg-OH or Arg-Arg-OH have been disclosed. These derivatives are produced as natural intermediates in the enzymatic conversion of proinsulin into insulin in vivo, and small quantities of them can also be detected in pancreatic extracts. The said residues are normally eliminated by trypsin and/or carboxypeptidase B, or enzymes having similar specificity, with liberation of unmodified insulin.

Further insulin derivatives having basic C-terminal modifications are disclosed, for example, in EP-A 132,770 and EP-A 140,084.

It is common to all these insulin derivatives that the additional positive charge(s) which is(are) located on the surface of the molecule confer on the molecule an isoelectric point which is displaced into the neutral range. Depending on the derivative, the isoelectric points measured by isoelectric focusing are from about 5.8 to about 8.5, in particular about 6.2 to about 8.2. This means that the derivatives are less soluble in the neutral range than is unmodified insulin, whose isoelectric point, and thus whose region of maximum insolubility, is at a pH of about 5.4, whereas it is normally in dissolved form in the neutral range.

Therapeutically interesting combinations are used, such as, for example, the mixture of insulin in dissolved form or in the form of NPH crystals or other classical prolonged forms+insulin derivative. It is possible in this way to prepare, inter alia, very long-acting products with different basal profiles. This is particularly desirable in the case of human insulin because, as experience to date has shown, its duration of action does not have a genuine ultraprolonged profile (such as, for example, the analogous beef insulin products) either in the form of zinc crystals or in the form of NPH crystals. These known formulations contain up to 1% zinc ions, but, in particular, not more than 0.8%, based on the mass of insulin/insulin derivatives. For crystallization it usually suffices to have relatively small amounts of zinc, of a maximum of only about 40 μg/100 international units (I.U.), but preferably not more than about 30 μg/100 I.U., which, in some circumstances, are already present in the dry substance. They may also contain auxiliaries having a delaying action on insulin release, such as globin or protamine sulfate.

Apart from the advantages in respect of crystal size and its homogeneity, the relatively low zinc content, which is below the concentrations at which zinc has to be regarded as the depot carrier, means that the crystal suspensions are freely miscible with dissolved insulin. Thus, it is possible, for example, to combine insulin solutions with suspensions of the insulin derivative crystals before administration.

It is possible by varying the proportions of the individual components to control the profile of action of the pharmaceutical obtained in this way.

Thus, crystal suspensions composed of the described derivatives have, in an advantageous manner, those properties which are desirable for the treatment of diabetes mellitus. The prolonging principle is intrinsic to the insulin derivatives and derives from a phenomenon of protein chemistry, the sparing solubility at the isoelectric point. The practical result is a true ultra-prolonged profile.

However, it is additionally desirable to have available not only the ultra-prolonged profile but also moderately prolonged profiles.

This object has been achieved according to the invention by producing and preparing new mixed crystals composed of A. unmodified insulin, des-Phe-B1 insulin, des-Thr-B30 (human) or des-Ala-B30 (beef, pork) insulin and B. at least one insulin having a basic modification at the C-terminal end of the B chain.

The substances suitable for component A are those having an isoelectric point less or equal to about 5.5; the insulins, having basic modifications, of component B are those having an isoelectric point between about 5.8 and about 8.5.

Compared with the known purely physical mixtures of the same individual components, and despite their comparable stability (with a zinc content which is zero or only low) the mixed crystals according to the invention show a distinct reduction in the extremely long duration of action, with a strength of action, as are used with classical depot insulin products (with protamine insulin crystals or 2-zinc insulin crystals), whose duration of action is shorter, for the treatment of diabetes mellitus. However, at the same time the duration of action is distinctly longer than with the classical depot insulin products; thus it is somewhere between the duration of action of the said classical depot insulin products and the extremely long duration of action of the purely physical mixtures of the individual components A and B. This effect is particularly desirable in the case of human insulin therapy, and has not hitherto been possible. It is extremely surprising that the mixed crystals according to the invention show this particular effect.

The necessary rapid onset of action of the insulin component A is not lost despite the mixed crystallization and can, if necessary, be accelerated by mechanical or physical mixing with dissolved insulin.

The unexpected and therapeutically extremely useful effect is probably brought about by the more ready solubility of the crystal lattice assemblage of the insulins B, having basic modifications, at physiological pH values following the specific incorporation of imperfections by means of component A having a lower isoelectric point.

The preferred ratio by weight of components A and B in the mixed crystals according to the invention is about (10–90): (90–10). This means that each of the two components A and B should normally be present to the extent of at least about 10% by weight in the mixed crystals.

Mixed crystal component A is unmodified insulin - principally human, pork or beef insulin -, des-Phe-B1 insulin (preferably human, pork or beef) and des-Thr-B30 human insulin or des-Ala-B30 (pork, beef) insulin. In general, component A is composed of only one representative of these insulins, with (unmodified) human insulin being preferred.

The mixed crystal component B is formed by at least one insulin having a basic modification at the C-terminal end of the B chain. Examples of suitable insulins having appropriate basic modifications of this type are the insulin derivatives corresponding to formula I in EP-A 132,769, EP-A 132,770 and EP-A 140,084. Preferred components B are Arg-B31 human insulin and $Arg_2$-(B31-32) human insulin.

The component B can be composed either of one or of several individual compounds. Virtually any desired mixture of the individual compounds, such as, for example, the two last-mentioned human insulin derivatives, is possible.

Furthermore, the components A and B in the mixed crystals are preferably from the same species (that is to say, for example, both human or pork).

Particularly preferred mixed crystals contain human insulin as component A, and Arg-B31 human insulin or $Arg_2$-(B31-32) human insulin, or any desired mixture of the latter, as component B.

It is possible according to the invention to obtain the mixed crystals composed of components A and B only from a solution having a rather narrow pH range; surprisingly, outside this narrow pH range no, or at least non-optimal, mixed crystals are obtained.

The process according to the invention for the preparation of these mixed crystals comprises preparing an aqueous solution composed of A. unmodified insulin, des-Phe-B1 insulin, des-Thr-B30 (human) or des-Ala-B30 (pork, beef) insulin, B. at least one insulin having a basic modification at the C-terminal end of the B chain, at least one physiologically tolerated preservative, at least one physiologically tolerated tonicity agent, at least one physiologically tolerated acid, and, where appropriate, other physiologically tolerated additives and auxiliaries, of pH from about 2.5 to about 3.5, and comprises the solution then being adjusted by addition of a physiologically tolerated base and, where appropriate, of a physiologically tolerated buffer, to a pH of from about 5.5 to about 6.9, preferably of from about 5.9 to about 6.5, and inducing the crystallization of the mixed crystals composed of components A and B from this solution.

The overall concentration of components A and B in the aqueous solution before crystallization can vary within a relatively wide range; however, a concentration between about 0.2 and about 40 mg/ml, in particular from about 1 to about 7.5 mg/ml, is preferred.

The components A which are preferably used are those having an isoelectric point less than or equal to about 5.5; suitable components B should have an isoelectric point between about 5.8 and 8.5.

Otherwise, the same statements as already made above in the description of the mixed crystals according to the invention apply to components A and B. The preferred component A is human insulin, and the preferred component B is Arg-B31 human insulin and/or $Arg_2$-(B31-32) human insulin. In the case where more than one representative of component B is used, it is possible easily to control the desired profile of blood glucose lowering by the mixing ratio of the component.

In turn, components A and B can in principle be in any desired mixing ratio; however, a ratio by weight of about (10–90):(90–10) is preferred. In this case, the ratio by weight of the components A and B found in the mixed crystals is the same as is set up in the initial solution.

It is possible to use as physiologically tolerated preservatives the agents which are customary and known for such purposes, that is to say, for example, aromatic hydroxy compounds such as phenol, m-cresol and/or p-hydroxybenzoic esters (of the latter mainly the ethyl ester) etc. The concentration of the preservative(s) should also be in the usual range. Appropriate concentrations are between about 0.02 and about 1% (by weight).

Suitable physiologically tolerated tonicity agents are likewise the compounds customary for such purposes, such as, for example, glycerol and/or NaCl, etc. Their concentration should also be in the usual range; i.e. that is to say in this case advantageously about 300 milliosmole/liter.

Examples of physiologically tolerated acids which are used (to adjust the pH) are acetic acid, citric acid, phosphoric acid etc. Their concentration essentially results from the limitation on the pH of the solution.

Examples of suitable physiologically tolerated bases are NaOH, KOH etc, and of physiologically tolerated buffers are sodium acetate, citrate or phosphate, tris(hydroxymethyl)aminomethane etc.

The crystallization solution may of course, where appropriate, also contain other physiologically tolerated additives and auxiliaries such as, for example, a Zn salt.

After the pH of the (initially rather acid) crystallization solution has been adjusted to about 5.5 to about 6.9, preferably from about 5.9 to about 6.5, the solution is left to stand at a temperature of, preferably, about 3° to 27° C., in particular of about 10° to 20° C.; the mixed crystals of A and B then crystallize out more or less rapidly.

Together with the supernatant solution, they can be directly used as appropriate pharmaceutical agents. If Zn ions (in the form of appropriate compounds) have been added as depot auxiliaries to the solution, the amount should preferably have been adjusted such that the resulting mixed crystal suspension contains up to about 100 μg/100 I.U. Zn ions. As a variant of this formulation, the mixed crystals produced in this way can also be isolated by centrifugation, after freeze-drying, be resuspended, appropriate for the dose, in a placebo buffer.

The mixed crystals of the invention, and the corresponding pharmaceutical formulations which contain these mixed crystals, are outstandingly suitable for the treatment of diabetes mellitus because of the moderately prolonged profile and the possibility of "fine control" by varying the nature and amount of, in particular, the individual compounds of component B.

The invention is now explained in more detail by the examples which follow.

Example 1

Mixed crystal suspension composed of 25% human insulin and 75% Arg$_2$-(B31-32) human insulin and having a total activity of 40 I.U./ml.

The following are dissolved in a total volume of 100 ml of H$_2$O

| Arg$_2$-(B31-32) human insulin (27 I.U./mg) | 111 mg |
|---|---|
| Human insulin (27 I.U./mg) | 37 mg |
| Citric acid monohydrate | 1050 mg |
| Glycerol | 1600 mg |

-continued

| Phenol | 65 mg |
|---|---|
| m-Cresol | 165 mg |

The pH of the solution is about 3.5.

The solution is adjusted with 1N NaOH to pH 6.3 for the crystallization. After crystallization has been completed at room temperature overnight, it is possible to detect in the supernatant, using HPLC (=high pressure liquid chromatography), −5% human insulin/Arg$_2$-(B31-32) human insulin. The ratio between them is, as it was in the cocrystallization, 25/75%; on s.c. (=subcutaneous) administration of 100 μl of the clear supernatant to a rabbit there is no significant or measurable lowering of blood glucose (because the solution now contains virtually no active substance).

Example 2

The following are crystallized together as in Example 1:

| Arg$_2$-(B31-32) human insulin | 74 mg |
|---|---|
| Arg-B31 human insulin (27 I.U./mg) | 37 mg |
| Human insulin | 37 mg |

The crystal sediment is centrifuged, washed with buffer and freeze-dried. The freeze-dried cocrystal powder is suspended in placebo buffer of pH 6.5 to produce 40 I.U./ml.

Example 3

| Human insulin (27 I.U./mg) | 37 mg |
|---|---|
| Arg-B31 human insulin (27 I.U./mg) | 111 mg | are crystallized together as in Example 2, isolated and freeze-dried. A suspension of the crystal powder in placebo buffer of pH 6.3 (40 I.U./ml) shows, when 0.2 I.U./kg is administered s.c. to a dog, a distinctly prolonged lowering of blood glucose, comparable with that by NPH insulin.

We claim:

1. Mixed crystals composed of consisting essentially of
    A. unmodified insulin, des-Phe-B1 insulin, human des-ThR-B30 pork des-Ala-B30 insulin or beef des-Ala-B30 insulin and
    B. An insulin having a basic modification at the C-terminal end of the B chain,
wherein the ratio by weight of the two components A and B is about 10–90:90–10.

2. Mixed crystals as claimed in claim 1, in which the isoelectric point of component A is less than or equal to about 5.5, and that of component B is about 5.8 to about 8.5.

3. Mixed crystals as claimed in claim 1, wherein component A is human insulin, and component B is selected from the group consisting of Arg-B31 human insulin, Arg$_2$-(B31-32) human insulin and a combination of Arg-B31 human insulin and Arg$_2$-(B31-32) human insulin.

4. A pharmaceutical composition containing an effective amount of mixed crystals as claimed in claim 1 for use in the treatment of diabetes mellitus, in a physiologically tolerated vehicle.

5. A method for treating a patient suffering from diabetes mellitus, which comprises administering to said patient a pharmaceutical composition as claimed in claim 4.

* * * * *

UNITED STATES PATENT AND TRADEMARK OFFICE
CERTIFICATE OF CORRECTION

PATENT NO. : 5,028,587
DATED : July 02, 1991
INVENTOR(S) : Michael DORSCHUG et al.

It is certified that error appears in the above-identified patent and that said Letters Patent is hereby corrected as shown below:

On the Title page

In the Abstract, Line 3, insert --at-- after "(b)"; and

Claim 1, Column 6, Line 46, change "ThR" to --Thr--.

Signed and Sealed this

Twenty-ninth Day of December, 1992

Attest:

DOUGLAS B. COMER

Attesting Officer      Acting Commissioner of Patents and Trademarks